United States Patent [19]

Wikel

[11] 4,309,258

[45] Jan. 5, 1982

[54] CONVERSION OF BENZIMIDAZOLE ISOMERS

[75] Inventor: James H. Wikel, Greenwood, Ind.

[73] Assignee: Eli Lilly and Company, Indianapolis, Ind.

[21] Appl. No.: 212,932

[22] Filed: Dec. 4, 1980

[51] Int. Cl.$^3$ .............................................. B01J 19/12
[52] U.S. Cl. ................................................. 204/158 R
[58] Field of Search ........................ 204/158 N, 158 T

[56] References Cited

U.S. PATENT DOCUMENTS 3,692,651  9/1972  Sletzinger ...................... 204/158 R

OTHER PUBLICATIONS

Tetrahedron Letters, 1979, 12, 1017–1020.
J. Org. Chem., 1962, 27, 4309–4312.
M. Orchin and H. H. Jaffe, Symmetry, Orbitals, and Spectra, Wiley–Interscience, N.Y. 1971, 321–324.

*Primary Examiner*—Howard S. Williams
*Attorney, Agent, or Firm*—Karen B. O'Connor; Arthur R. Whale

[57] ABSTRACT

A method of isomerization is disclosed which converts the anti isomer of 1-isopropylsulfonyl-2-amino-6-(α-hydroxyiminobenzyl)benzimidazole to the syn isomer using photolysis.

4 Claims, No Drawings

CONVERSION OF BENZIMIDAZOLE ISOMERS

BACKGROUND OF THE INVENTION

A number of substituted benzimidazole compounds have been discovered that display unusually good antiviral activity, see for example U.S. Pat. Nos. 4,008,243; 4,018,790; 4,118,573; and 4,118,742. Among the most active of such benzimidazole antiviral agents are two oximes, which are the syn and anti isomers of 1-isopropylsulfonyl-2-amino-6-(α-hydroxyiminobenzyl)benzimidazole. These oximes are especially active against rhinoviruses that cause upper respiratory infections. The separation of the syn and anti oximes is described in U.S. Pat. No. 4,191,832.

Although the anti isomer of 1-isopropylsulfonyl-2-amino-6-(α-hydroxyiminobenzyl)benzimidazole is more potent than the syn isomer, the syn isomer is more bioavailable. Therefore, it is critical to have one isomer in essentially pure form depending upon the characteristic desired. It is an object of this invention to provide a method for converting a mixture of syn and anti isomer or pure anti isomer to the syn isomer using photolysis.

SUMMARY OF THE INVENTION

This invention provides a method of isomerization which comprises irradiating the anti isomer of 1-isopropylsulfonyl-2-amino-6-(α-hydroxyiminobenzyl)benzimidazole in an organic solvent with a light source, which has a monochromatic wavelength of at least 280 nm to about 350 nm to form the syn isomer of 1-isopropyl-2-amino-6-(α-hydroxyiminobenzyl)benzimidazole.

DETAILED DESCRIPTION OF THE INVENTION

The preparation of the compounds used in this invention, the syn and anti isomers of 1-isopropylsulfonyl-2-amino-6-(α-hydroxyiminobenzyl)benzimidazole, is described in U.S. Pat. No. 4,118,742, which is incorporated by reference. This method of preparation forms a mixture of the syn and anti isomers of the oxime, which can be separated, if desired, by the technique described in U.S. Pat. No. 4,191,832, also incorporated by reference.

Once the benzimidazole compounds are prepared, the method of this invention is carried out by suspending a mixture of syn and anti isomers or pure anti isomer in an organic solvent. The anti isomer must be at least partially soluble in the solvent. Since the syn isomer is more soluble than the anti isomer, it dissolves upon formation and goes into solution. Suitable solvents include alcohols such as ethanol, propanol, and isopropanol; nitriles such as acetonitrile; chlorinated solvents such as chloroform, methylene chloride, dichloroethane, and 1,1,2-trichloroethane; and others, such as ethyl acetate, dimethoxyethane, and tetrahydrofuran. Any such solvent can be used; however, the solvent should be inert to the light source. The preferred solvents are dichloroethane and 1,1,2-trichloroethane. The amount of organic solvent is not a critical factor, except sufficient solvent should be used to completely suspend the oxime. If desired, the solvent and oxime can be heated to a temperature from about 20° C. to about 80° C. to facilitate dissolution. In addition, it is preferable to remove any oxygen that may be present before irradiation.

Once the solution is prepared, it is irradiated with a light source. The source must emit a monochromatic wavelength of at least 280 nm to about 350 nm. Preferably the wavelength is from about 310 nm to about 350 nm. The more monochromatic is the wavelength, the faster and cleaner is the conversion. Such light sources include mercury lamps, fluorescent tubes, sunlight, sunlamps, and the like. The use of sunlight and sunlamps will work as light sources in this invention, but the reaction is slower, does not go to completion, and has more decomposition products. The preferred source, however, is fluorescent tubes.

Although a certain intensity is not required, the rate of syn isomer formation is directly proportional to the intensity of the light source. The amount of time required to irradiate and form the syn isomer depends upon the percentage of syn isomer desired, and the intensity of the light source. For example, at an intensity of about 2-4 watts, the rate of syn formation is about 50% complete in about 1 hour, about 60% complete in about 6 hours, about 75% complete in about 12 hours, and about 80% complete in about 16 hours.

Once the isomerization or conversion is completed to the stage desired, the syn isomer can be recovered. This recovery can be accomplished as described in U.S. Pat. No. 4,191,832.

The following example describes the present invention. The example is illustrative of the invention, but is not to be construed as limiting the invention.

EXAMPLE

A solution-slurry of 7.6 g of a mixture of anti and syn isomers (49.4% anti/49.6% syn with ca. 1% impurities) 1-isopropylsulfonyl-2-amino-6-(α-hydroxyiminobenzyl)benzimidazole as the monohydrate in 710 ml (1 Kg) of 1,1,2-trichloroethane is irradiated at 350 nm in a Rayonet reactor (fluorescent tubes lamp, Southern New England Ultraviolet Co.) at an intensity of 2-4 watts. Nitrogen is bubbled through the solution before and during irradiation to eliminate the oxygen in solution.

After 16 hours, a precipitate is filtered that weighs 4.13 g (54% yield). HPLC indicates that the precipitate is about 97% syn. The filtrate is concentrated under reduced pressure to have a residue. (The pressure is reduced in order to lower the boiling point of the solvent to about 35°-40° C. and facilitate removal.) About 300 ml of methylene chloride is added to the residue with stirring and then the mixture is chilled. A precipitate is collected that weighs 2.02 g (26% yield).

A HPLC analysis of the methylene chloride filtrate indicates that about 92% is the syn isomer. The mass spectrum of both precipitates shows the expected molecular ion at m/e=358.

The NMR spectrum (dimethylsulfoxide) indicates that the first precipitate is the 1,1,2-trichloroethane solvate. The following elemental analysis is obtained:

Calc. for $C_{19}H_{21}N_4O_3SCl_3 \cdot H_2O$: Theory: C, 44.75; H, 4.51; N, 10.99; Cl, 20.90. Found: C, 44.29; H, 4.21; N, 11.15; Cl, 19.84.

The NMR spectrum (dimethylsulfoxide) indicates that the second precipitate is the dichloromethane hemisolvate. The following elemental analysis is obtained:

Calc. for $C_{17}H_{18}N_4O_3S \cdot \frac{1}{2} CH_2Cl_2$: Theory: C, 52.43; H, 4.74; N, 13.98; Cl, 8.86. Found: C, 52.93; H, 4.55; N, 13.63; Cl, 7.75.

The first precipitate is 96.99% syn; 2.48% anti; and 0.54% impurities, while the second is 91.89% syn; 7.13% anti; and 0.99% impurities.

I claim:

1. A method of isomerization which comprises irradiating the anti isomer of 1-isopropylsulfonyl-2-amino-6-(α-hydroxyiminobenzyl)benzimidazole in an organic solvent with a light source, which has a monochromatic wavelength of at least 280 nm to about 350 nm, to form the syn isomer of 1-isopropylsulfonyl-2-amino-6-(α-hydroxyiminobenzyl)benzimidazole.

2. The method of claim 1 wherein the organic solvent is ethanol, dichloroethane, or 1,1,2-trichloroethane.

3. The method of claim 2 wherein the light source is a mercury lamp or fluorescent tube.

4. The method of claim 3 wherein the wavelength is from about 310 nm to about 350 nm.

* * * * *